United States Patent [19]

Dechene et al.

[11] Patent Number: 5,408,181

[45] Date of Patent: Apr. 18, 1995

[54] NMR SYSTEM FOR MEASURING POLYMER PROPERTIES

[75] Inventors: Ronald L. Dechene, Boxford, Mass.; Thomas B. Smith, Atkinson, N.H.; David R. Day, Charlestown, Mass.; Christian I. Tanzer, Bedford, Mass.; Scott A. Marino, Haverhill, Mass.; Ronald J. Tache, Malden, Mass.; Ajoy K. Roy, Danvers, Mass.

[73] Assignee: Auburn International, Inc., Danvers, Mass.

[21] Appl. No.: 113,833

[22] Filed: Aug. 30, 1993

[51] Int. Cl.$^6$ .............................. G01R 33/20
[52] U.S. Cl. .................... 324/307; 324/300
[58] Field of Search ............ 324/300, 318, 315, 322, 324/307, 309

[56] References Cited

U.S. PATENT DOCUMENTS

| | | | |
|---|---|---|---|
| 2,864,995 | 12/1958 | Shoolery | 324/300 |
| 3,621,378 | 11/1971 | Kleiman | 324/307 |
| 4,254,373 | 3/1981 | Lippmaa et al. | 324/321 |
| 4,266,194 | 5/1981 | Hlavka | 324/315 |
| 4,489,275 | 12/1984 | Sancier et al. | 324/318 |
| 4,587,492 | 5/1986 | Landermilch | 324/318 |
| 4,940,942 | 7/1990 | Bartuska et al. | 324/321 |
| 5,015,954 | 5/1991 | Dechene et al. | 324/307 |
| 5,049,819 | 9/1991 | Dechene et al. | 324/307 |
| 5,122,745 | 6/1992 | Smith et al. | 324/307 |
| 5,192,910 | 3/1993 | Hepp et al. | 324/318 |
| 5,300,888 | 4/1994 | Webster et al. | 324/315 |
| 5,302,896 | 4/1994 | Dechene et al. | 324/307 |
| 5,321,358 | 6/1994 | Mohr et al. | 324/307 |

FOREIGN PATENT DOCUMENTS

0156394  7/1991  Japan ...................... 324/315

Primary Examiner—Sandra L. O'Shea
Assistant Examiner—Raymond Y. Mah
Attorney, Agent, or Firm—Edwin H. Paul; Jerry Cohen

[57] ABSTRACT

A pulsed nmr analysis system for polymers materials extracted from industrial processes at a mobility enhancing temperature (at or above glass transition temperature for amorphous polymers, at the crystalline transition temperature for crystalline and semi-crystalline polymers). The sample is measured via nmr techniques and results correlated to viscosity and melt index or melt flow (which are related to average molecular weights). The nmr system (in or out of resonance) includes: sample throughput system (P, LI, V1, V2) and user system controls (104) to establish digitized free induction decay curves (C), from which components functions are determined using linear or non-linear regression techniques to correlate the curve components to the target nuclei and to flow rates in plastics. Substantial improvement of correlation of nmr derived constants and equations of a free induction decay curve with the foregoing polymer properties is obtained via (1) conducting the nmr process at a mobility enhancing temperature (normally elevated compared to the industrial process temperature of the industrial process) and (2) holding temperature substantially constant at such elevated temperature.

6 Claims, 11 Drawing Sheets

NMR SYSTEM FOR MEASURING POLYMER PROPERTIES

CROSS REFERENCE TO RELATED PATENTS AND APPLICATIONS

This application is closely related to the U.S. Pat. No. 5,015,954 issued on 14 May 1991 to Dechene et al., and to U.S. Pat. No. 5,049,819 issued Sep. 17, 1991 to Dechene et al., both entitled "MAGNETIC RESONANCE ANALYSIS IN REAL TIME, INDUSTRIAL USAGE MODE"; and to U.S. patent application 07/794,931 filed Nov. 20, 1991 entitled "IMPROVED MAGNETIC RESONANCE ANALYSIS IN REAL TIME, INDUSTRIAL USAGE MODE" now U.S. Pat. No. 5,302,896; to U.S. patent application Ser. No. 07/885,633 filed May 19, 1992, entitled "NMR ANALYSIS OF POLYPROPYLENE IN REAL TIME" now U.S. Pat. No. 5,302,897, to U.S. patent application, Ser. No. 07/959,739, filed Oct. 13, 1992, entitled "REAL TIME MAGNETIC RESONANCE ANALYSIS WITH NON-LINEAR REGRESSION MEANS" now U.S. Pat. No. 5,319,308 to U.S. patent application, Ser. No. 07/961,264, filed Oct. 15, 1992, entitled "APPARATUS TO OBTAIN FLOW RATES IN PLASTICS VIA FIXED FREQUENCY, PULSED NMR" (still pending), and to U.S. patent application, Ser. No. 08/075,799, filed Jun. 14, 1993, entitled "THERMAL CONTROL FOR SAMPLE UNDER TEST IN AN ON-LINE NMR SYSTEM" (abandoned). All of these patents and patent applications are of common assignment with this application, and the disclosures of all are hereby incorporated herein by reference, as though set out at length herein.

FIELD OF THE INVENTION

The present invention effects property measurements made on a sample of polymer material by repetitively generating a nuclear magnetic resonance (nmr) free induction decay (FID) curve. The physical parameter(s) to be measured is (are) related to the precession and relaxation of nuclei (hydrogen protons) of the sample under test. The nmr measurement is performed while maintaining the sample at or about a specific controlled temperature. More particularly, the present invention relates to carrying out the measurement at or above the "glass transition" temperature (Tg) for amorphous polymers, and at or above the "crystalline transition" temperature (Tα) but below the "melting temperature" (Tm) for both crystalline and semi-crystalline polymers. Herein Tg, Tα and Tm are defined as temperatures where the following physical phase transitions take place. At the glass transition temperature (Tg), the fractional free volume for amorphous polymers increases appreciably and the polymer chains start undergoing rapid, almost isotropic motion. Amorphous polymer at this temperature has not melted and still retains a solid-like appearance to the lay observer. This state is sometimes referred to, in the art, as "rubbery". As a result, the nmr parameters, including time constants (T2's), are influenced. This enables better correlation with viscosity and melt index or melt flow. For both crystalline and semi-crystalline polymers it is necessary to carry out nmr measurements at or above the crystalline transition temperature (Tα) in order to influence the nmr parameters and obtain better estimations of viscosity and melt index or melt flow. In the case of a semi-crystalline polymer, the melting and crystalline transition temperatures are greater than the amorphous glass transition temperature. Adjusting the sample temperature to such temperatures as just described enhances nmr precision and reliability for the above measurements and for other physical property measurements performed via nmr techniques. The specific temperatures as they relate to specific polymers are found in handbooks and textbooks common in the art, for example, TEXTBOOK OF POLYMER SCIENCE, published by Wiley-Interscience, a Division of John Wiley and Sons, Inc., second edition (1971), by Fred W. Billmeyer, Jr. The above temperatures will, collectively, be referred to hereinafter, excepting for specific instances for clarity, as the "mobility enhancing temperature". This definition is a minimum or threshold temperature. There is a temperature range extending above the "mobility enhancing temperature" where the benefits occur without the sample handling problems associated with molten polymers.

The present invention relates to nmr measurements of molecular weight where the sample is not reduced to a liquid state; instead, the temperature of the sample is held where the sample remains solid but the nuclear mobility (see below) is enhanced.

Not only is the temperature held essentially constant at the mobility enhancing temperature during the measurement and handling of a single sample, but, if needed, each sample is brought to the controlled mobility enhancing temperature prior to nmr measurement and stabilized there for the ensuing nmr measurement.

The invention particularly concerns industrial, essentially on-line use of nmr/FID data extraction with repetitive multiple sampling from a manufacturing or transport process or the like and feedback (or feed forward) to process control, but is applicable to off-line laboratory analysis.

BACKGROUND OF THE INVENTION

The analysis methods described herein and in the above related patents and applications use a pulsed burst or pulse of energy that is designed to excite the nuclei of a particular nuclear species of a sample being measured (the protons, or the like, of such sample having first been precessed in an essentially static magnetic field); in other words the precession is modified by the pulse. After the application of the pulse there occurs a free induction decay (FID) of the magnetization associated with the excited nuclei. That is, the transverse magnetization associated with the excited nuclei relaxes back to its equilibrium value of zero. This relaxation produces a changing magnetic field which is measured in adjacent pickup coils. A representation of this relaxation is the FID curve.

The analysis methods described herein and in the above related patents and applications are to decompose the FID waveform into a sum of separate time function equations. The coefficients of these equations are derived from the FID by use of a Marquardt-Levenberg (M-L) iterative approximation that minimizes the Chi-Squared function—a technique well known in the art. Some of the time function equations found useful are: Gaussians; exponentials; Abragams, defined herein by $(Gaussian)*(sin(t))*(1/t)$; modified Gaussian, defined herein by $((Gaussian)*(cos(sqrt(t))))$, and trigonometric. From these time functions a set of parameters is calculated. Some of these parameters are ratios of the y-axis intercepts, decay times (or time constants of decay) for each of the time curves, and the cross products and reciprocals thereof. Statistical modeling techniques are used to select a subset of these terms to form a regression model, and regression coefficients are computed for this subset.

But, relating these previously mentioned parameters, quantitatively and qualitatively, back to the species of target nuclei is required. In the above referenced patent applications, the system is calibrated with known samples, and a regression equation is generated which relates the parameters to the types, properties and quantities of the target nuclei. An unknown sample is introduced, the time functions are derived via the M-L iteration, and the parameters are calculated. The parameters are "regressed" via the regression equation to yield the types, properties and quantities of target nuclei in the unknown sample. That is, the measured parameters from the unknown FID are used with the regression equation, and the types, properties and quantities in the unknown sample are determined. It is to be understood that the multidimensional regression equation may not be graphically represented, and that the regression equation may be non-linear. As a simple regression technique example, consider that the grade point average of each of the students at a college were related to that student's SAT score and high school standing (forming a three dimensional space). The line formed is a "regression line" (which may be graphed). A new student's grade point average may be predicted by placing the student's SAT and high school standing on the "regression line" and "reading" the grade point average.

The sample temperature may form the basis for another regression parameter. It is therefore necessary to carry out nmr measurements with the sample at a certain pre-fixed temperature. This is handled by controlling the temperature of the sample. A limitation exists since any temperature difference between the sample and the sample chamber and the local environment will cause the sample temperature to change during the measurement. This changing temperature creates errors in the nmr results which may become significant—particularly in industrial, essentially on-line usage (e.g., manufacturing or transport processes or the like with repetitive sampling and feedback or feed forward process control). Such errors have been observed, for example, when measuring and then predicting the solids content in processed cheese, and, similarly, various melt flow rate measurements in polyolefins, such as melt index (MI), flow rate ratio (FRR) and melt flow (MF).

It is well established that the T2 relaxation rate in solutions or melts is directly dependent on the viscosity of the solution or melt. Polymer viscosity measurements, in either solution or melts, can therefore be performed by nmr measurements and since viscosity is related to the average molecular weight of polymers, a correlation between T2 and molecular weight can be established.

In the solid phase, however, the restricted molecular motion shortens the T2 value dramatically, and in the extreme of crystalline or near rigid amorphous polymers the T2 values are very short and show no indication of yielding molecular weight information.

Care must be taken when measuring and controlling sample temperature. Probes, infrared devices and other known temperature measuring devices for on-line temperature measurements need to be designed and constructed to not materially interfere with setting and maintaining a given sample temperature. Accordingly, it is an object of this invention to provide a thermal environment where a sample under test is maintained at a controlled settable temperature.

It is an object of this invention to effect a sample measurement of polymer materials at a mobility enhancing temperature that enhances precision and reliability for viscosity, molecular weight, melt index and melt flow. Herein, molecular weight, melt index and melt flow, are closely related. It is another object of this invention to measure the temperature change of the sample and adjust heater means such that there is essentially no sample temperature change during the nmr measurement time period. Another object of this invention is to gain the benefit of the higher mobilities of polymers and the enhanced nmr response which is found when polymer material is melted but without actually melting the material. It is another object of this invention to maintain the sample chamber temperature about equal to the mobility enhancing temperature of the successive samples such that the successive samples will maintain about the same temperature during the nmr measurement time period. It is to be understood that the process temperature may change slowly with time as a function of ambient temperatures or process conditions.

Another object is to correlate known viscosities and/or melt index or melt flow (which are related to average molecular weights) with the measured nmr parameters at or around the mobility enhancing temperature for amorphous polymers, crystalline polymers and semi-crystalline polymers (see below). Such correlations are used to determine the calibration coefficients for predicting unknown viscosity and/or melt index or melt flow for an unknown sample.

SUMMARY OF THE INVENTION

The above objects are met in a system that takes a series of samples from an on-line flowing system, measures the sample temperature at the start and at the end of a measurement time period, and adjusts (by heating or cooling) the temperature of the sample until the sample temperature stabilizes at or around a target level (the mobility enhancing temperature). The sample is placed in a sample chamber and an air curtain (as found incorporated in patent application Ser. No. 08/075,799) controls the sample temperature and will accommodate small variations in the incoming sample temperature. There is essentially no sample temperature change between the start and the end of the measurement time period. On subsequent sample measurements the sample temperature is monitored and any temperature change beyond a given value may result in that sample being discarded. Restabilization may then be necessary. Baseline temperature restoration may be required from sample to sample.

Temperature stabilization is met by immersing the sample in a thermal environment that matches the sample temperature, thereby eliminating thermal gradients. In a preferred embodiment the sample is extracted from the process and fed into a heated chamber (not the sample chamber—where the nmr measurement takes place). The desired temperature for the specific heated material is known and the temperature of the heating chamber wall is maintained above that temperature to ensure that the sample is at about the desired temperature. Heated air or a gas, like nitrogen, is introduced into the sample directly to "fluidize" and ensure that the sample uniformly contacts the heated chamber walls. Depending on the particular design, either the heated walls or the heated nitrogen may be the primary source of heat to bring the sample to the desired temperature. The sample remains in the heated chamber long enough to guarantee that the desired temperature is achieved. The sample is then introduced into the sample measuring chamber where the nmr measurement will occur. This sample measuring chamber tube is surrounded with temperature controlled air (an air curtain), and in turn the air curtain is surrounded by a second temperature controlled zone. In a preferred embodiment the sample temperature is measured by any of a variety of means, including but not limited to: semiconductor junctions, thermocouples, thermistors, or infrared sensors. The temperature is measured at two different times during the sample resident time (at the start and at the end of a measurement in a preferred embodiment) in the sample chamber. The air curtain temperature is incrementally adjusted at the end of each nmr measuring cycle so as to force the change in sample temperature to approach zero during the next nmr measuring cycle. If the air curtain temperature is maintained equal to the sample temperature, no heat energy will flow between the sample and the air curtain and the sample temperature during measuring will remain constant. The assumption that the next sample will be at essentially the same temperature as the preceding sample is valid for virtually all on-line operations wherein this invention may be used.

Other objects, features, and advantages will be apparent from the following detailed description of preferred embodiments taken in conjunction with the accompanying drawing(s) in which:

DETAILED DESCRIPTION OF PREFERRED EMBODIMENTS

Figures 1A, 1B:
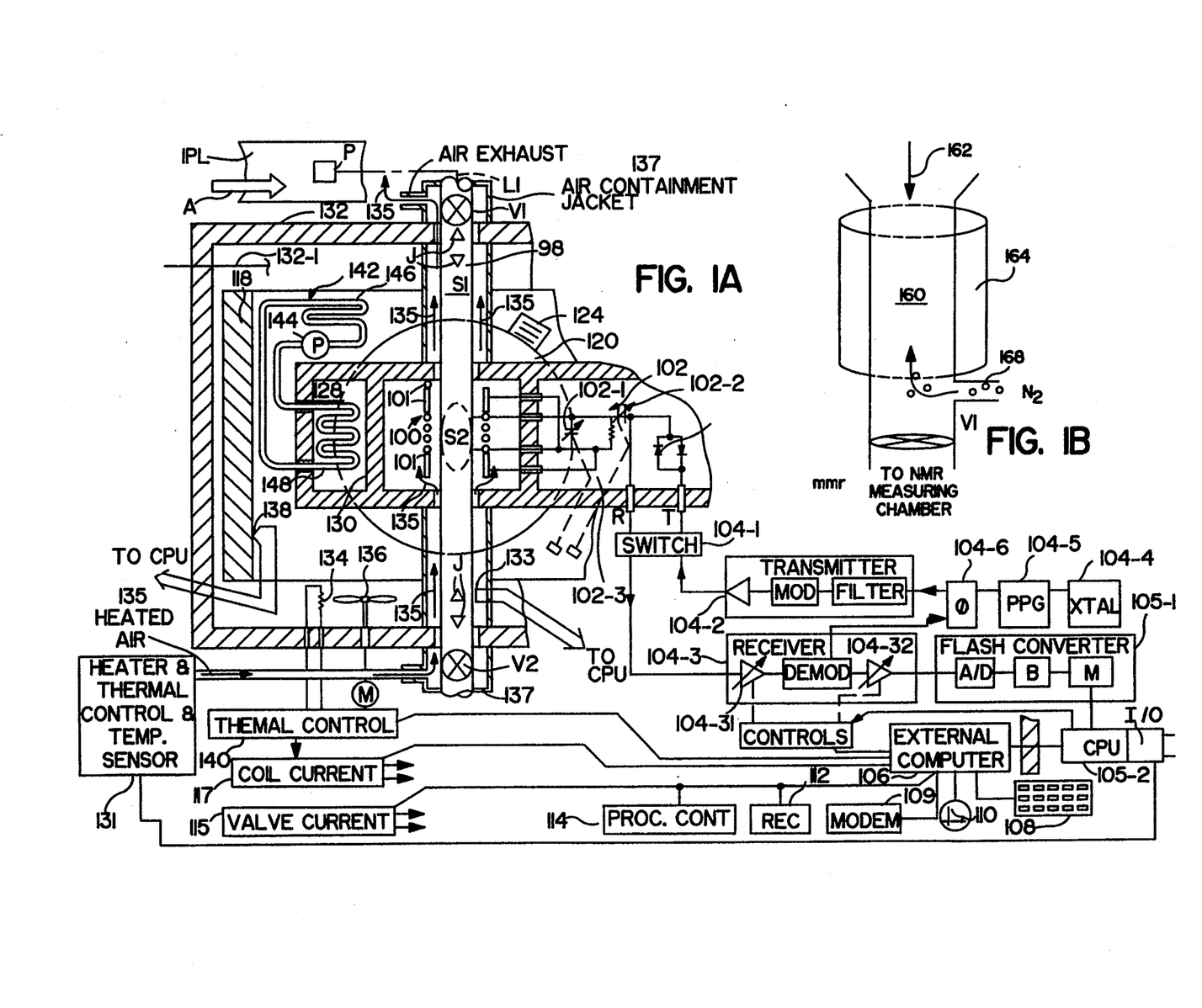
FIGS. 1A, 1B and 1C are block/schematic drawings of a preferred embodiment of the invention, a pulsed nmr system suitable for measuring a range of polymer materials.

FIG. 1A shows transverse and cross sections, with block diagram inserts, of an nmr apparatus and method where the present invention may be used to advantage. An industrial process line IPL has material flowing as indicated by arrow A. Some of the material is captured by a probe P and fed through an inlet line LI to a sample region S1. The region is defined by a tube 98 typically about 30 cm long made of an essentially non-magnetic, nonconducting material which does not itself generate substantially interfering FID signals (glass, certain ceramics, certain plastics or hybrids may be used). The sample region is defined between inlet and outlet valves V1 and V2. Gas jets J are also provided. These are pulsed on/off repeatedly to agitate fluent sample materials during sample admission and expulsion. The region S2 is the critical portion of the sample. It is surrounded by a sample coil 100 tuned to resonance and driven by a tuning circuit 102 and related transmitter/receiver controller 104. Grounded loops 101 are Lenz Law shields which are provided above and below coil 100 to help shape the field of coil 100—i.e., contain the field established by an excitation pulse. The controller 104 includes an on-board microprocessor and required power supply elements, memory, program and I/O decoding suitable to interconnect to the hardware shown and to an external microcomputer 106 with keyboard 108, monitor (or other display) 110, recorder 112 and/or process controller 114 (to control the process at IPL). The operator initiates and controls operation from the display keyboard 108 and the resulting data and signals are subsequently shown on the display 110 and utilized in 112 and/or 114. The computer 106 also controls instrument operation conditions.

The region S2 of tube 98 and coil 100 are in a static, but adjustable, crossing magnetic field defined by a magnetic assembly 116 which comprises a yoke 118, pole pieces 120, surrounding Helmholtz coils 124, and a coil current generator 117. The critical sample region S2 of the tube 98 and magnet are contained in a metallic (but non-ferromagnetic) box 126 with highly thermally conductive face-plates 128 and internal partitions 130 and over-all mass related to each other to minimize harmonics and other interferences with a signal emitted from coil 100 to a sample and/or returned from the sample for pick-up by coil 100 and its tuned circuit 102 and transmit/receive controller 104.

Figure 1C:
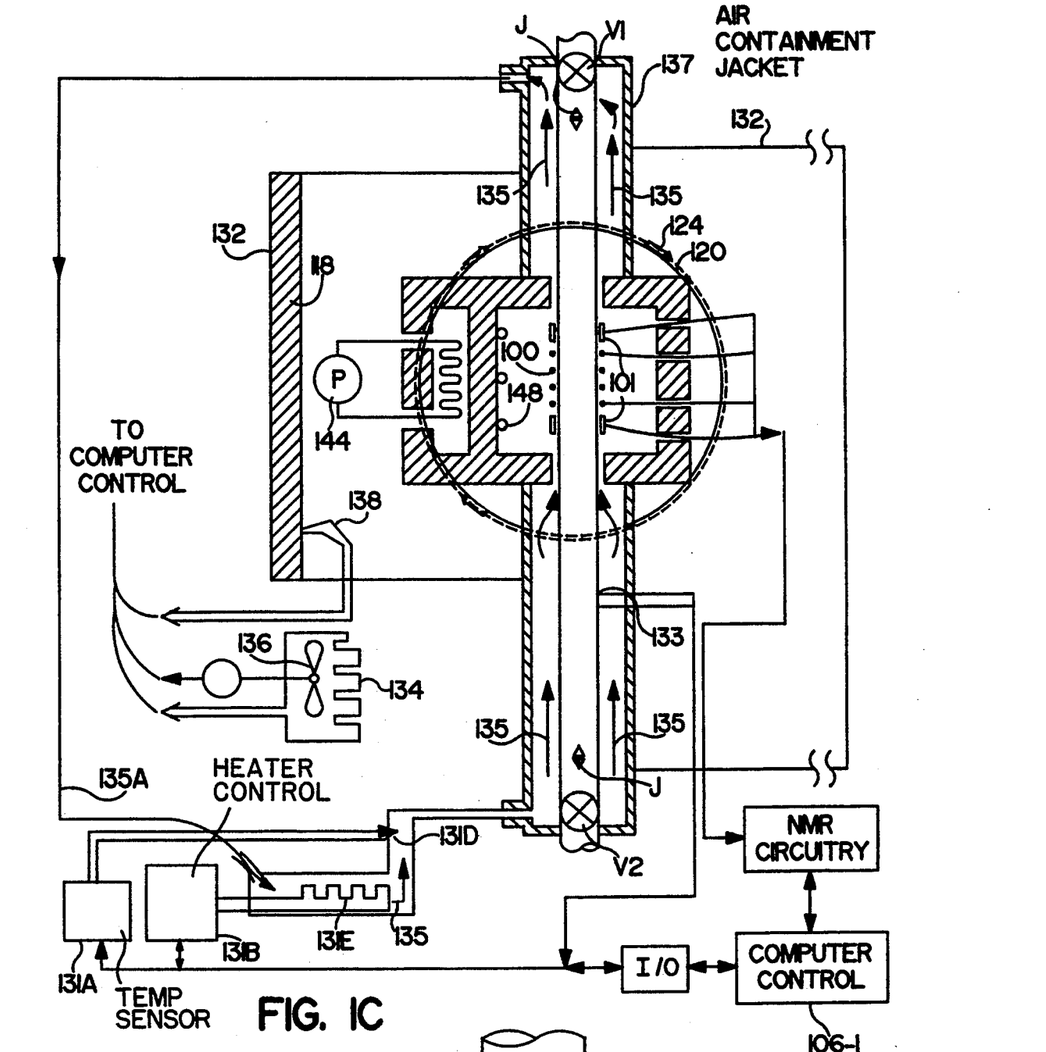

The magnetic assembly, including yoke 118, and other parts therein as shown on FIGS. 1A and 1C, is in turn contained in an environmental control chamber 132 with optional inert gas fill and purge controls (not shown), an internal electrical heater 134, a motor M driving fan 136, and a temperature sensor 138 in the air stream whose temperature is reflective of the temperature at pole pieces 120 and in the region surrounding the air curtain containment jacket 137. Additionally there is a heated chamber shown in FIG. 1B where the sample is heated prior to introduction into the nmr sample chamber. A thermal controller 140 processes temperature signals from 138 to adjust heating/circulation at 134/136 as a coarse control and to adjust current through the Helmholtz coils 124 at magnet pole pieces 120 as a sensitive and fast fine control, as well as implementing general control instructions of computer 106. Further thermal stabilization is provided by a temperature controlled air curtain consisting of temperature controlled air 135 circulating inside an air containment jacket 137, completely surrounding the sample region under nmr measurement. The temperature of the air curtain is controlled by the heater thermal control 131B and temperature sensor 131D via 131A according to control parameters received from CPU 105-2(I/O). Sample temperature is measured by temperature sensor 133 from which an external computer system 106 determines the desired air curtain temperature set point to be conveyed to heater thermal control 131B.

FIG. 1B is a schematic outline of the heating chamber 160. The sample is fed (as indicated at arrow 162) into the chamber. There is a heating element 164 surrounding the chamber with its temperature set about 10 or so degrees centigrade higher than the mobility enhancing temperature known for the specific material. The temperature may be looked up in the aforementioned text. The material remains in the chamber long enough to ensure that the sample has achieved the proper temperature. The temperature need only be within a few degrees of an actual set point. To further ensure proper and uniform heating, a heated temperature controlled nitrogen stream of gas 166 or air is introduced via a port 168 in order to fluidize the material. After two (or more) minutes the sample is introduced into the nmr measuring chamber S2 by opening the valve V1. The gas is introduced in a direction and with a pressure to create a turbulence in the material that induces movement of particles and homogenization of material temperature.

Figure 2:
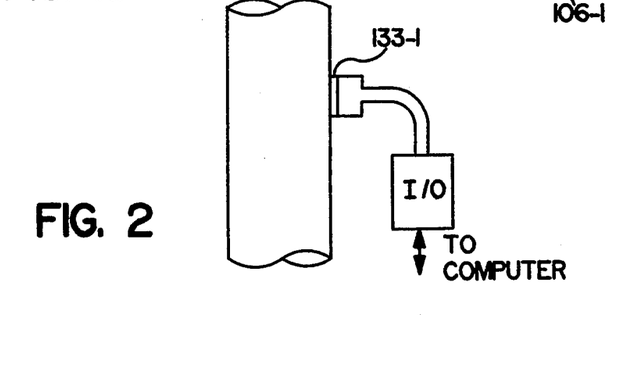
FIG. 2 is a detail showing the sample temperature measurement.

In FIG. 1C all the electronics and computers and other elements of the system controler are grouped for simplicity of description into one block 106-1. The temperature of the sample chamber is measured by a temperature sensor 133, a silicon junction device or thermocouple, embedded in the chamber wall. FIG. 2 shows another preferred embodiment where the sensor is an infra-red (heat) sensor with a window through the sample chamber wall whereby heat radiation impinges the sensor. The sensor signal is fed through an I/O (input/output) interface to the computer portion of the controller 106-1. In another preferred embodiment the I/O interface may contain an A/D converter separated from the computer and/or input to the computer via some other communication port, e.g., a serial port. The computer can interrogate the sensor and measure the temperature at any time, typically at the start of the nmr measurement time period and again at the end. In response to a temperature change during the nmr measurement, the system adjusts the temperature through the heater 131E. The temperature of the heated air 135 is measured by the sensor 131D placed in the air path 135. The controller 106-1 has control of maintaining the sample temperature constant through the heated air within the air curtain. These two means give the entire system the ability and capacity to maintain the sample temperature essentially constant while the environmental air around the nmr system changes.

Still referring to FIG. 1C, the computer control system maintains the temperature of the sample constant during the nmr measurement period via: (a) measurement of the sensor 138 and control of the heater 134 and fan 136; (b) the circulation system 144, and (c) the air curtain. In operation the system is calibrated by measuring the temperature of the sample by sensor 133. The temperature is sent to the computer portion of controller 106-1. The temperature of the sample at the end of the measurement period is measured and if there has been a temperature change of the sample, the system, via means (a), (b) and (c) above, changes the temperature environment of the sample chamber. The process occurs on each successive sample in order to minimize or eliminate sample temperature change during the nmr measuring period.

As discussed before, to enable better correlation of the nmr data with viscosity and melt index or melt flow (average molecular weight), amorphous polymers are measured at or above the glass transition temperature; crystalline and semi-crystalline polymers are measured at or above the crystalline transition temperature but below the melting temperature.

EXAMPLE

Three solid phase polyvinyl chloride (PVC) samples, with a Tg from 70° C. to 90° C., were obtained from a commercial source. The samples' molecular weights were: 300K, 166K and 68K.

Figure 3A:
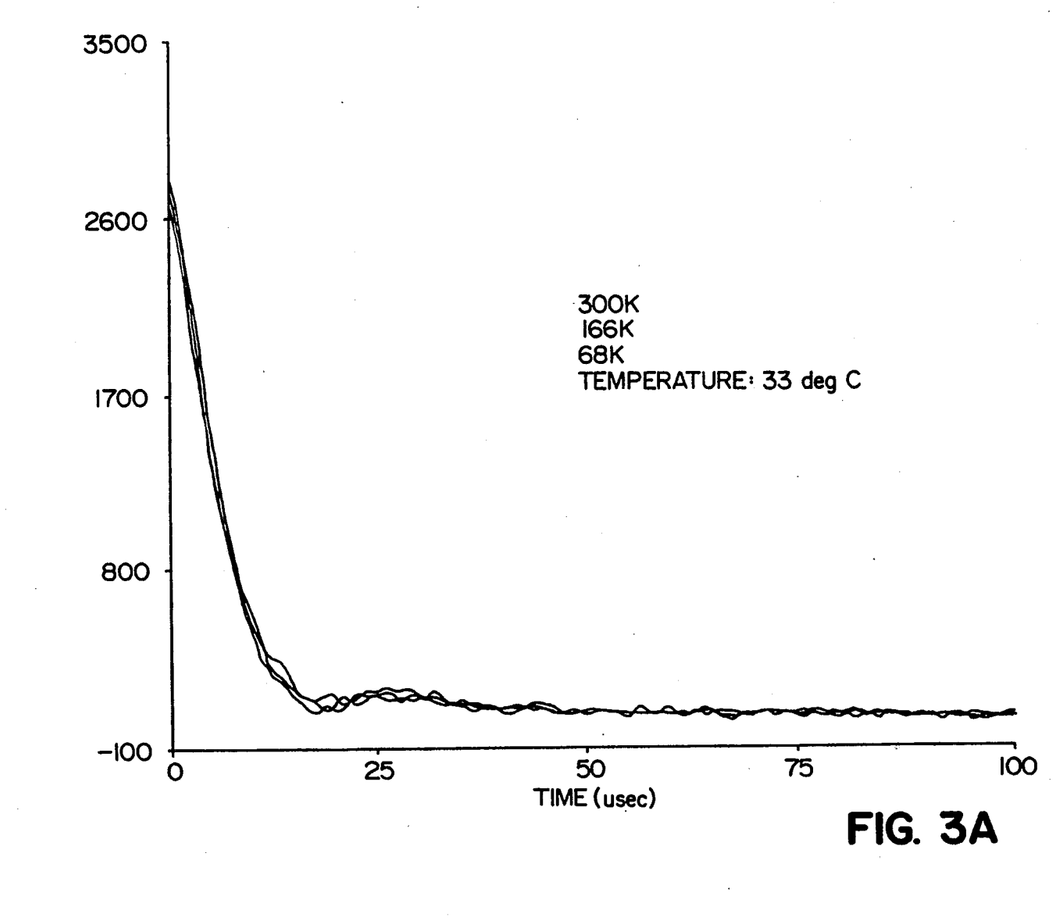
FIG. 3A, 3B, 3C and 3D are graphs related to the example.

With reference to FIG. 3A, the above samples were measured at 33° C. (well below the minimum Tg temperature) in an nmr instrument as described in this disclosure. The graph of FIG. 3A shows that all three samples had nearly identical time responses, and each such response achieved its final level in about 15 microseconds. The graphs indicate no distinction even with large differences in molecular weight. This result shows that at 33° C. molecular weight differences cannot be detected from measurements in the solid phase and, thus by inference, nmr measurements cannot correlate with viscosity measurements.

Figure 3B:
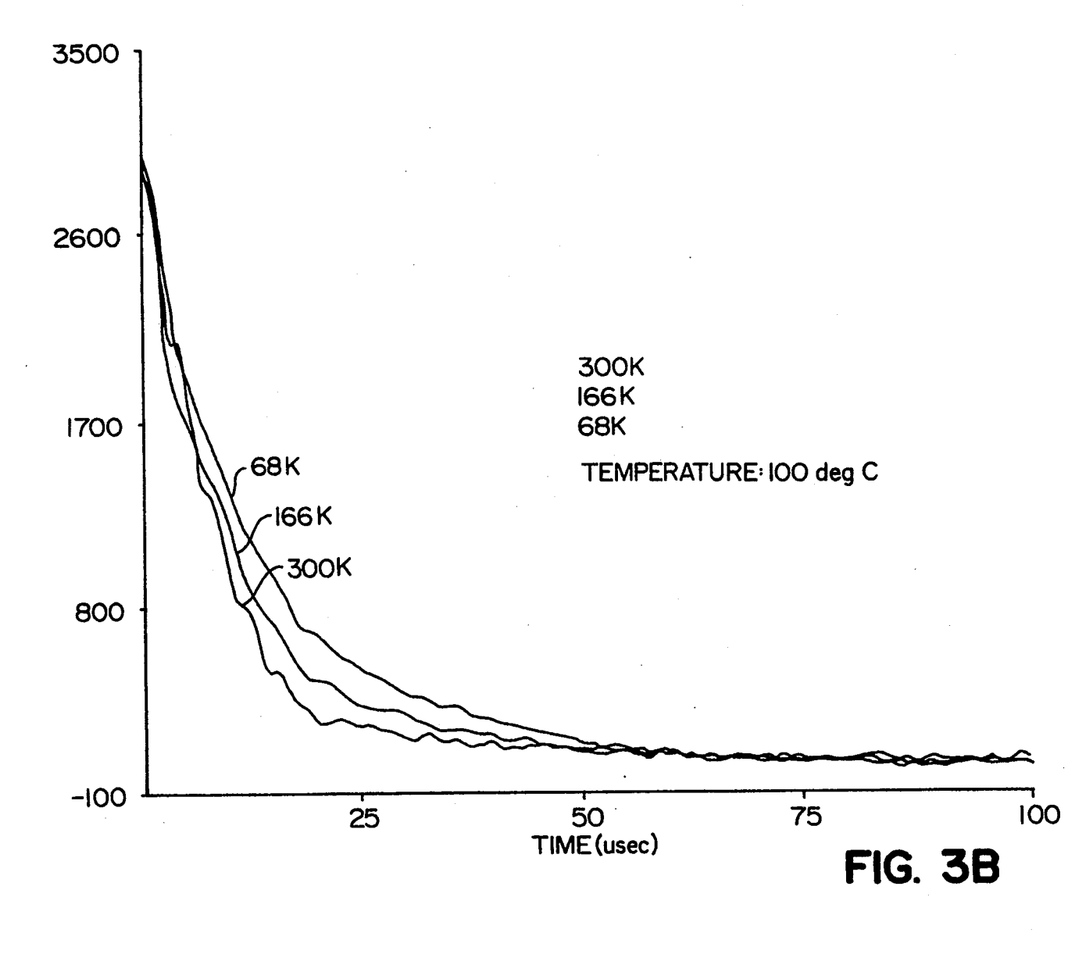

When the samples are heated to 100° C., quite different results are shown in the graph of FIG. 3B. In this graph the three curves are clearly distinct from each other and the decay times are clearly shorter for the larger molecular weight samples.

Table A summarizes the results of this example:

TABLE A

| MOLECULAR WEIGHT | T2 at 33° C. | T2 at 100° C. |
|---|---|---|
| 68K | 6.6 μsec | 14.5 μsec |
| 166K | 6.7 μsec | 11.7 μsec |
| 300K | 7.3 μsec | 9.13 μsec |

Figure 3C:
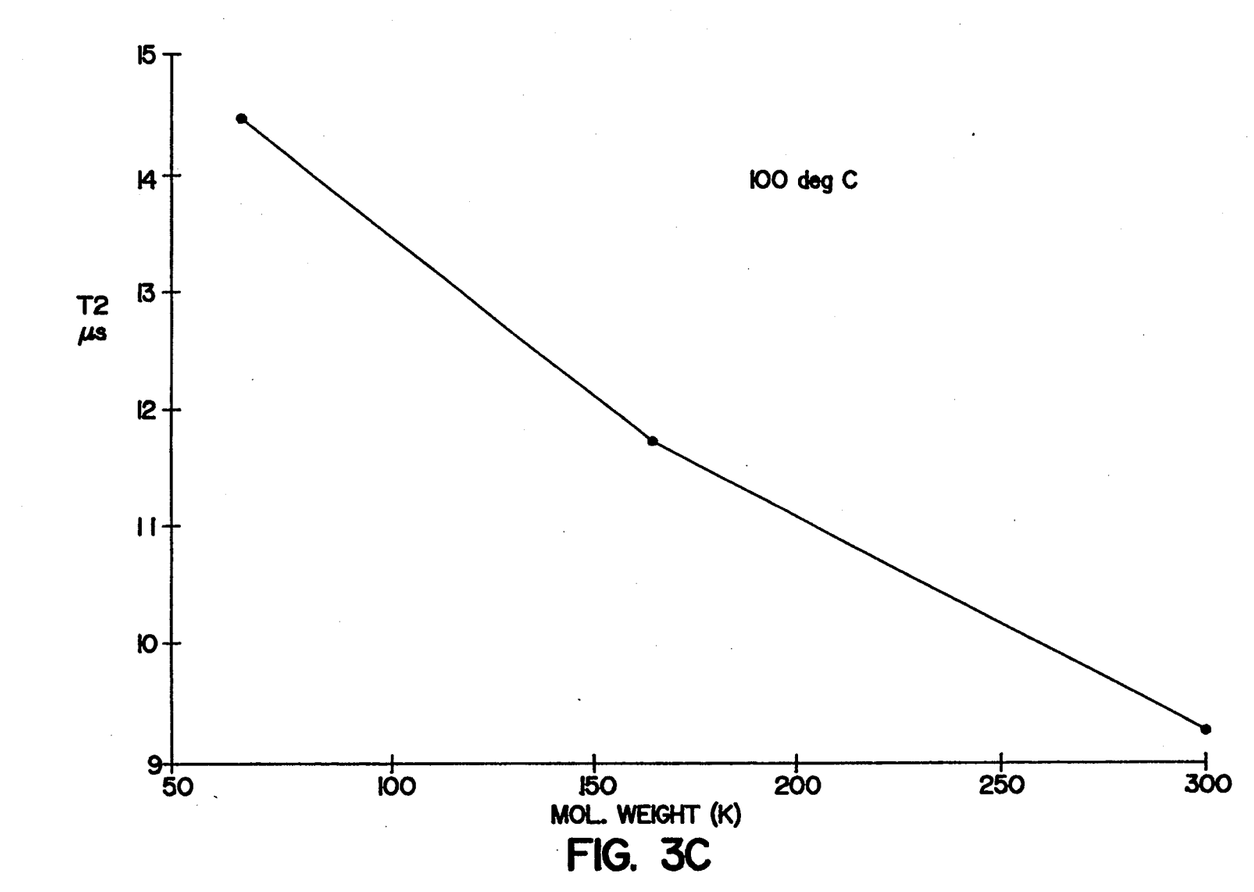

FIG. 3C is a graph of Table A data at 100° C.

Figure 3D:
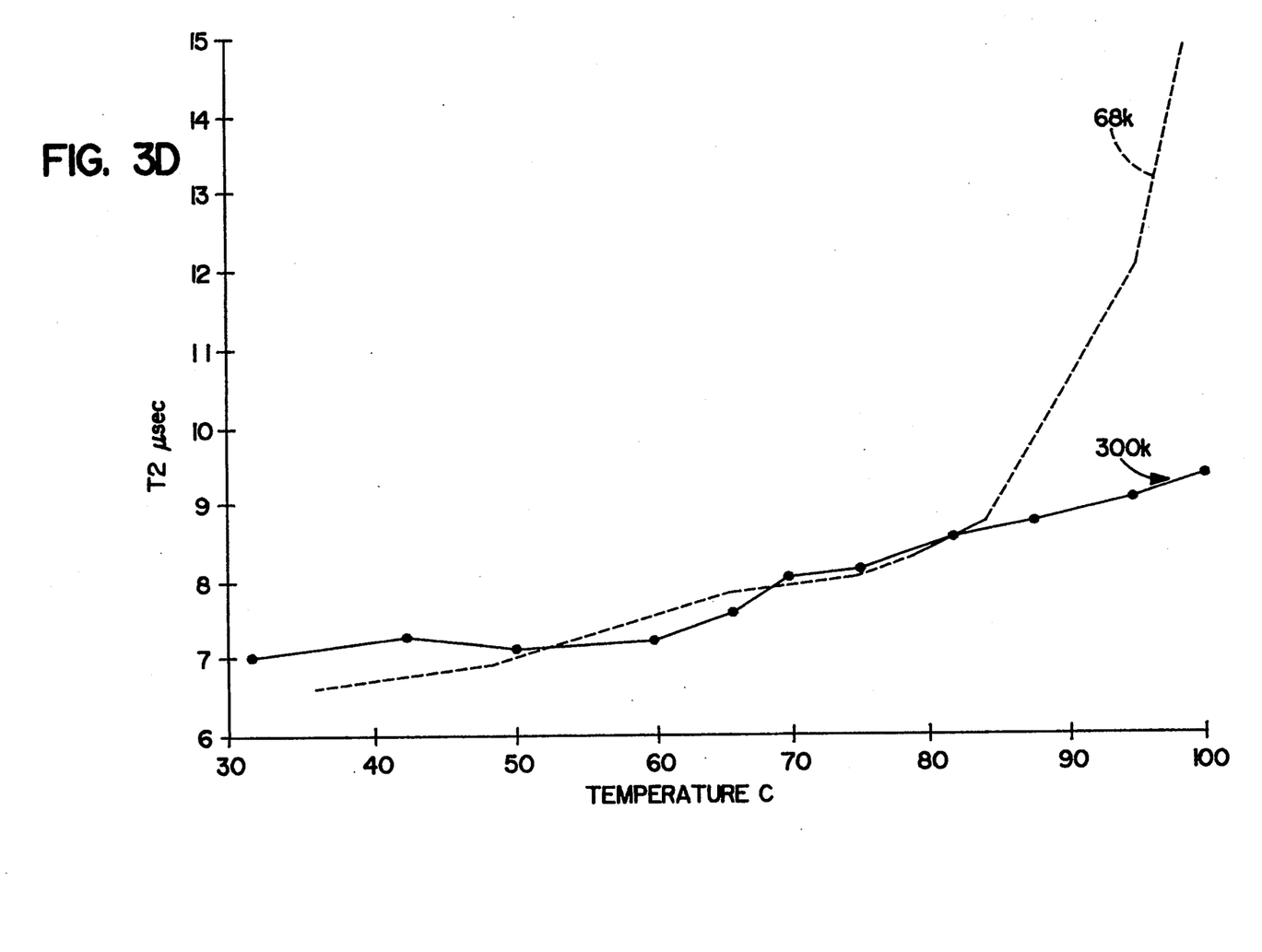

FIG. 3D is a graph for the 68K and 300K samples showing the increase in T2 with increasing temperature. It is especially obvious that as the temperature increases the T2 for the lower molecular weight material dramatically increases compared to the higher molecular weight material and thus serves to distinguish the two materials (as might be expected).

Referring back to FIG. 1A, the strength, consistency and constancy of the magnetic field between poles 120 in the region S2 of the sample is thus controlled by a uniform base magnetic field modified by a small correction generated by Helmholtz coils 124 in the entire region S2. The Helmholtz coils 124 are energized by the coil current controller 117 to accurately trim the final magnitude of the field in which the sample is placed. This field is the vector addition of the fields due to the magnet poles 120 and the Helmholtz coils 124. The controller 117 sets the current through the Helmholtz coils 124 using current generators. The coils 124 are wound around the magnet pole pieces such that the magnetic field created by the current in the coils 124 can add to or subtract from the field created by the magnet pole pieces. The magnitude of the current through the coils 124 determines the strength of the field added to or subtracted from the field due to the magnet pole pieces (and related yoke structure) alone.

The actual determination of the current through the Helmholtz coils is accomplished by carrying out the magnetic energy and resonance techniques hereinafter described in preliminary runs and adjusting Helmholtz current until the maximum sensitive resonance is achieved, and then setting the Helmholtz current off resonance by a given offset, of about 0.1-3 KHz. In another preferred embodiment the system is operated at resonance.

The major elements of electrical controls are tuner 102, including coils 100 and 101 and variable capacitors 102-1 and 102-2, resistor 102-3 and diodes 102-4 and constructed for tuning to Q of twenty to sixty to achieve coil 100 resonance, and control 104 including a transmit/receive switch 104-1, a transmitter 104-2 and receiver 104-3, a crystal oscillator 104-4, gated pulse generator (PPG) 104-5, and phase shifter 104-6. The crystal provides a nominal twenty Megahertz carrier which is phase modulated or demodulated by the MOD, DEMOD elements of transmitter 104-2 and receiver 104-3. The receiver includes variable gain amplifier elements 104-31 and 104-32 for operation. The analog signals received are fed to a high speed at least 12 bit flash A/D converter 105-1 and internal (to the instrument) CPU element 105-2, which provides data to an external computer 106 which has a keyboard 108, monitor 110, modem 109, recording elements 112 and process controller elements 114, e.g., for control of valves V1, V2 via valve controls 115 and/or to coil current controls 117, all via digital-analog converters (not shown).

The analog signal FID curve is conditioned by a Bessel filter which acts as a pre-filter and an anti-aliasing filter as the subsequent sampling is usually done at 10 MHz. After digitization, the signal may be time smoothed by a Fast Fourier transform, Savitsky-Golay or other filter program. The combination of these filters produces a relative improvement in signal to noise ratio which enhances the accuracy of the system.

The excitation of coil 100 and excitation-precession of the sample's proton content and subsequent relaxation/decay produces a received FM signal that, after demodulation, controlled gain amplification, and A/D conversion produces the free induction decay (FID) curve.

As indicated earlier, preferred embodiments are found in any nmr instruments whether operated in resonance or out of resonance, including those preferred embodiments found in the above patents and patent applications which have been incorporated by reference into this disclosure. The following preferred embodiment describes a system and apparatus for the analysis of polymers, in particular, polypropylene and polyethylene.

Figure 4:
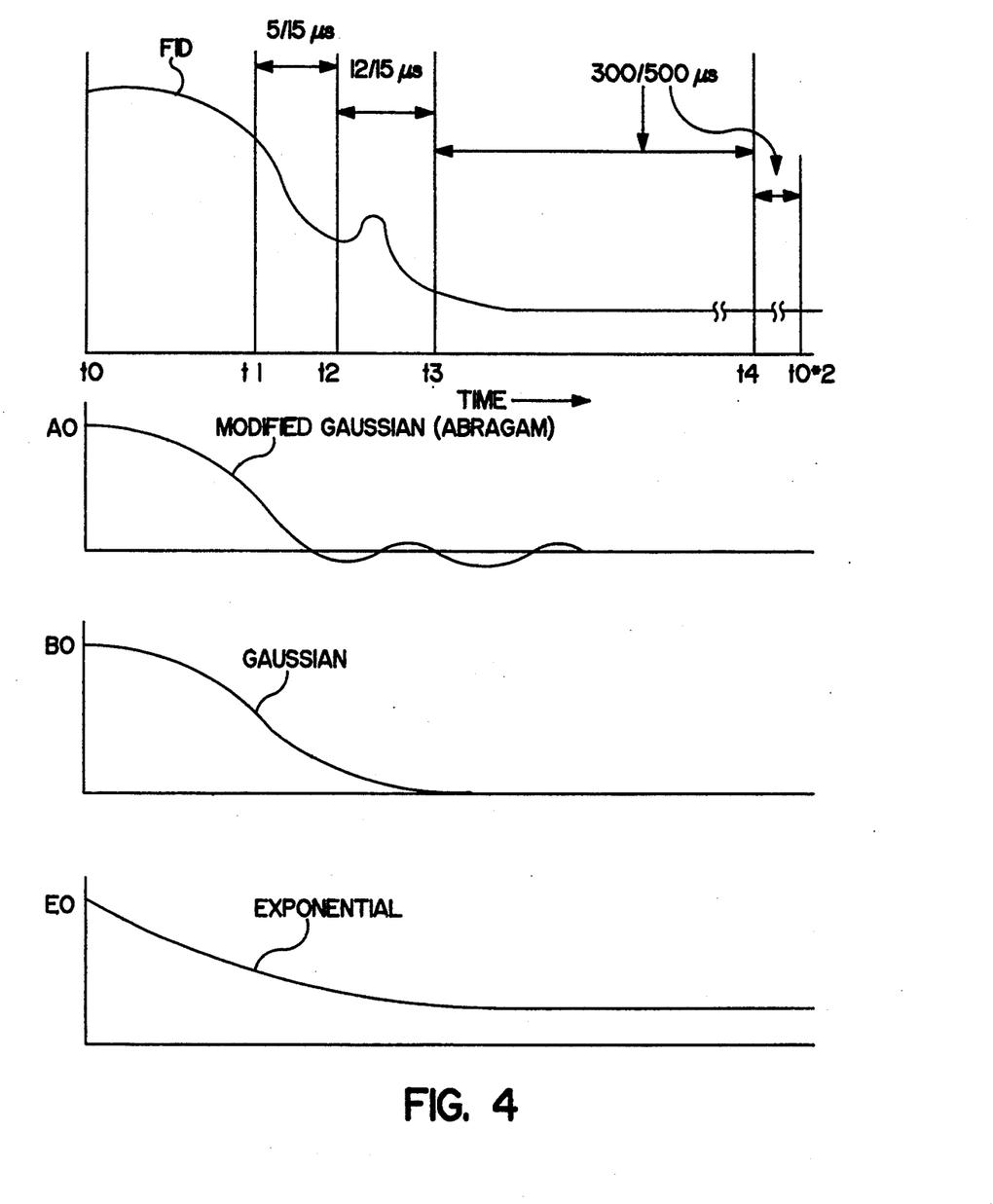
FIG. 4 is a graphical representation of an FID and its component curves measured for polyethylene.

Referring to FIG. 4, the digitized FID curve data for polyethylene or polypropylene, respectively, are transmitted to the external computer 106 where a program finds the best coefficients of the component curves to fit each digitized FID curve. In this preferred embodiment there are three component curves, a modified Gaussian, a Gaussian, and an exponential. Other preferred embodiments have more or less than three component curves and other curve types. The determination of the types of curves which make up the FID curve is important because, once the curves are known, they can be extended back to a time origin (shown as $A_0$, $B_0$ and $E_0$ at $t_0$, i.e., excitation of a Cycle 1), which is close to the center of the transmitted burst signal. This is important since there are saturation effects of the instrument's electronic gear which occur during and immediately after the excitation burst signal. During this time, measurements cannot be accurately taken, yet the region of interest under the curve, which is a measure of the number of nuclei in the sample, extends from the immediate end of the excitation burst to where the curve is too small robe digitized or it is in the noise.

The entire curve is decomposed into component curves and these curves are fitted to the data by an iterative process based upon the Marquardt-Levenberg (M-L) approximation technique applied automatically through a structured realization in software. This M-L technique is used to determine the magnitude of all the parameters, constants, frequencies, etc. which best fit the FID curve. M-L is an iterative technique where the entire curve is determined at once. The M-L iteration process performs the curve fitting by attempting to minimize the Chi-Squared error function (the sum of the squared differences between the measured data points and the data points from the derived equation). The results of the M-L approximation are accepted if the Chi-Squared error is small enough; if not, the M-L fitting procedure may be reapplied with a different set of starting assumptions. If this process also fails, the sample is discarded and a new sample obtained. The M-L technique is documented in the following references: *Ind. Appl. Math.*, vol. 11, pp. 431–441 by D. W. Marquardt, 1963; *Data Reduction and Error Analysis for the Physical Sciences* (New York, McGraw Hill), Chapter 11 by Philip R. Bevington, 1969; and *The State of the Art in Numerical Analysis* (London: Academic Press, David A. H. Jacobs, ed 1977), chapter III.2 by J. E. Dennis. As applied to the measurement regime of interest herein, in a preferred embodiment of the present invention, the selected parameters taken from the derived curves are the y-axis intercept ratios, time constants, frequency terms and other parameters described below.

Other known-in-the-art iterative techniques which may be applied instead of or with the Marquardt-Levenberg, include: Gauss-Newton and "steepest descent" (found in the above J. E. Dennis reference), Newton-Raphson (known in the art), "partial least squares", or like techniques, including combinations of these techniques.

One of the major difficulties in making use of iterative curve fitting techniques (such as Marquardt-Levenberg) is their tendency to reach incorrect solutions. Such solutions frequently (but not always) contain parameters which would imply a negative quantity of protons or an exponential "decay" which grows with time. These incorrect solutions lead to serious errors in the result found for a physical sample, for example, the density or flow properties (e.g. melt index) in polyethylene or the extent of tacticity or melt flow in polypropylene.

The usual methods of handling these difficulties have been:

(1) have a human evaluate the result and eliminate those solutions that are theoretically impossible, and/or (2) put a series of upper and lower bounds on each parameter beyond which the fitting procedure is forbidden to go.

In an on-line situation where readings are generated every few minutes, the first approach obviously cannot be used, and in the case of polyethylene and polypropylene the second approach fails because the bounds for each parameter depend on the actual values of the other parameters (note that, for polypropylene and polyethylene, the model equations involve ten or more parameters).

As discussed herein, the techniques to find a property of an unknown sample include calibration by applying the M-L technique to reach solutions for a group of FIDs from samples with known properties. The various amplitudes and time constants in the solutions are combined to produce a number of ratios, cross products and higher order parameters. These parameters may undergo various non-linear transformations and are finally regressed multi-dimensionally to obtain the coefficients of the regression equation to use in predicting a property of an unknown sample, say, for example, density. Each of the parameters contributes to the overall prediction of density. However, in the nature of things, these parameters tend to be correlated among themselves; e.g., a large crystalline content must necessarily correspond to a small amorphous content (comparing the Abragam to the exponential in the polyethylene FID solution). This means that overlapping density information is contained in many of the parameters used in the regression equation. Similar arguments apply to other properties, such as tacticity extent and melt flow in polypropylene.

To make use of this correlation (continuing the density example), the parameters are divided into subgroups (two roughly equal groups in a preferred embodiment) and each of these groups is regressed on density to obtain two further predictions of density based on each subgroup, as follows:

D1 (density)=F(subgroup 1)
D2 (density)=G(subgroup 2)

Because of the correlation, discussed above, among the parameters, the functions F and G (above) result in predictions D1 and D2 which are only slightly less accurate than the density prediction based on the entire set of variables. The ratio (MRR) or the difference (MRD) are formed as follows:

MRR=D1/D2=F/G
MRD=D1−D2=F−G

MRR has a nominal value of one and MRD zero. MRR and MRD are sensitive measures of whether or not a particular proposed M-L solution for an unknown sample belongs to the set of (calibrated) data from which the functions F and G were derived. If the calculated ratio or difference of D1 and D2 for a proposed M-L solution for fitting the FID of an unknown sample lies outside reasonably well-defined limits (usually +/−3 sigma), the proposed M-L solution may be assumed to be bad and is discarded.

Once the equation of the FID curve is known, each component curve can be extrapolated back to the midpoint of the excitation signal to establish the intercept of each said component curve.

The resulting data utilized in the computer 106 (FIGS. 1-2) is the equation for the FID curve as composed of a number of component curves. Each of these curves (and their intercepts) has been experimentally and theoretically related to particular nuclei of interest. In particular, when the FID curve equation is determined, the ratios of the y-axis intercepts, the cross product and squares of these ratios and the decay times for each of the curve components, the product temperature and a cosine term form a multidimensional model.

Calibration of the system is accomplished by measuring a number of known samples and using the M-L technique to derive the model equation constants associated with each known sample. Various non-linear transforms may then be applied to these constants, usually with the goal of linearizing their relationship to the dependent (i.e., predicted) parameter. Useful non-linear functions include exponential, logarithmic, powers and cross products of the independent (i.e., measured) parameters.

Figure 5:
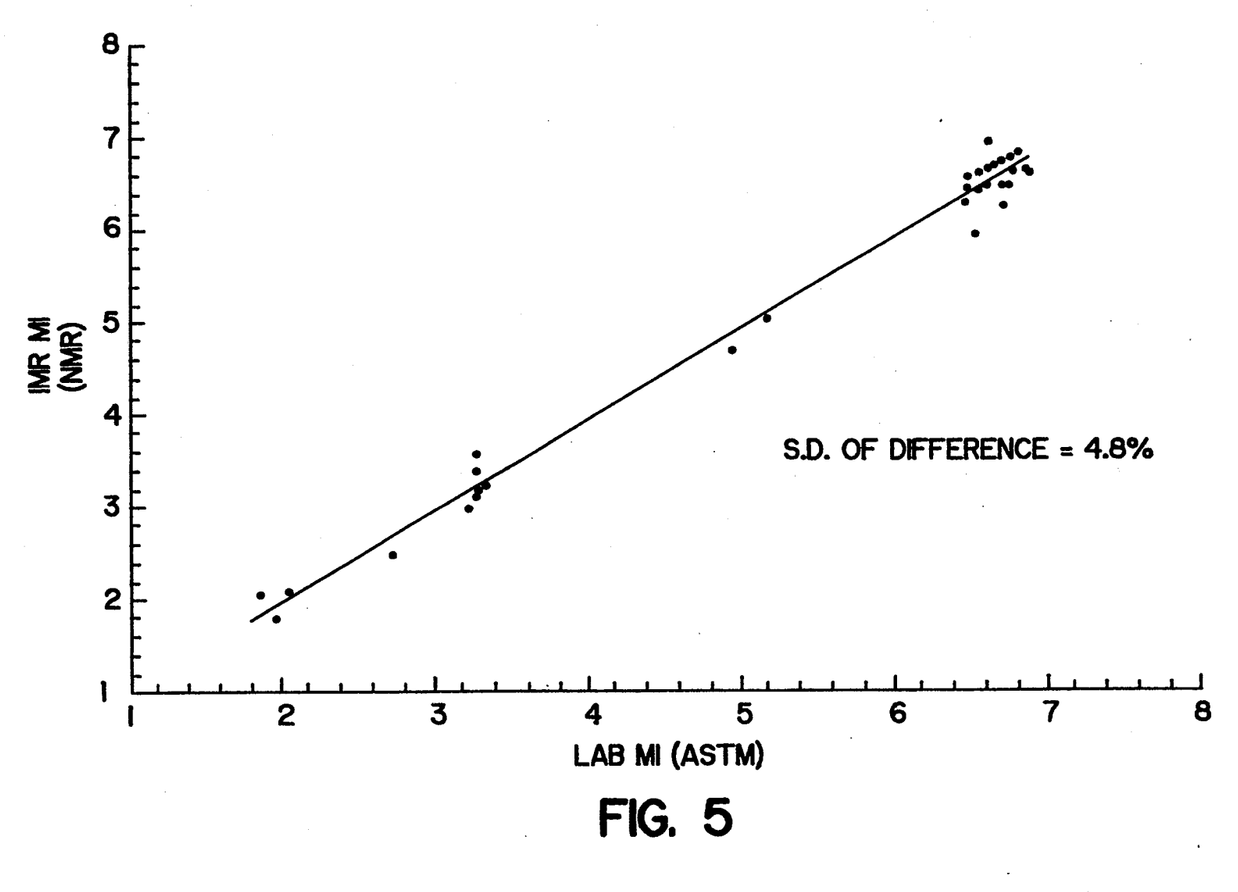
FIG. 5 is a graph of nmr measurements of MI compared to ASTM laboratory measurements of MI.

FIG. 5 is a graph showing on-line MI results of the nmr method compared with the laboratory ASTM MI method. The nmr MI results were determined from the FID analysis and model equations as noted previously. The standard deviation between the nmr MI and the ASTM MI is 4.8%. This standard deviation includes errors due to both the nmr and ASTM measurement methods. Calibration of the system is accomplished by measuring a number of known samples and using the M-L technique to derive the model equation constants associated with each known sample. The particular steps of one preferred embodiment are shown in FIG. 6A.

Figure 6A:
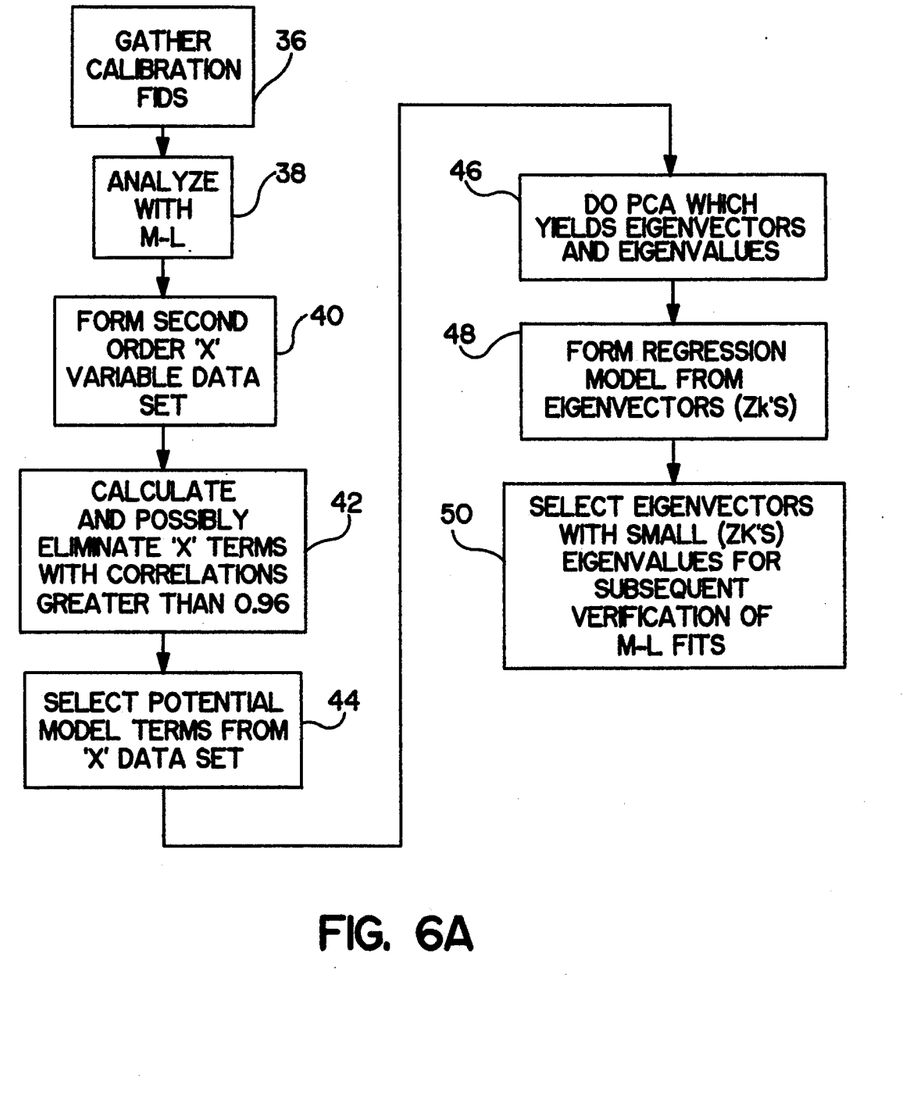
FIG. 6A and 6B are flow charts of a preferred embodiment of the present invention.

Referring to FIG. 6A, the first step 36 is to measure samples with known types, properties and quantities of target nuclei, including flow rates in plastics (MI, MF and FRR in polyethylene and polypropylene). This data gathering may be done on-line or off-line. The FID curve is digitized via a flash converter of at least 12 bits accuracy and stored in computer memory. The next step 38 is to apply the M-L iterative process to derive curve coefficients from the FIDs to a given Chi-Squared error. In step 40, the second order 'x' variables, the explanatory variables, are formed, e.g., ratios of Y-axis intercepts, squares and cross products of these ratios, decay times, and temperatures. Higher order combinations of these parameters may be calculated. These 'x's can be thought of as vectors in a multidimensional space where the space dimension is equal to number of the explanatory variables. If there is no multicollinearity among the 'x' data, the vectors are orthogonal in this space (i.e., all dot products are zero). As multicollinearity increases, the vectors move away from orthogonality. In the extreme case there may be perfect correlation between two or more of the 'x' variables and the vectors will lie on top of one another. An attempted regression analysis of such data would generate singular correlation matrices. The difficulties with highly correlated data 44 are eliminated by Eigenvalue (PCA) analysis (described below).

Next a set of potential explanatory variables ('x's) are chosen by stepwise or other known techniques 42. In this preferred embodiment three different sets of 'x' explanatory variables are selected and taken through the entire remaining steps and the set giving the best results is used. In this preferred embodiment the best result is that which results in the lowest adjusted standard deviation of error on the degrees of freedom. One set is composed of all the 'x' variables, the second set is formed by the known stepwise technique of adding each new variable and determining if that variable helped, and then continue adding those variables that help. The technique is also applied in a backwise fashion where each previously added variable is retested in the presence of each new variable. The third set is formed by taking all independent variables and variables with correlations between selected low and high limits, usually 0.2 to 0.96.

The next step is to perform a principal component analysis (PCA) 46. In step 44, potential explanatory variables, the 'x' data, are selected from the M-L derived time equations, including second and higher orders of these variables. As referred to earlier, it is expected that the 'y's (the independent variable) or characteristics of interest for the sample are related by a set of linear equations to these explanatory variables. However, every linear regression model can be restated in terms of a set of orthogonal explanatory variables, where these new variables are linear combinations of the original explanatory variables. These new explanatory variables are called principal components and are orthogonal, thus eliminating the problem of multicollinearity. The regression model equation using the original explanatory variables is:

Eq. 1 $Y = X\beta + u$, where Y is an nx1 column matrix of n observation, X is an nxp matrix of n observations on p explanatory variables, $\beta$ is a px1 column matrix of regression coefficients and u is an nx1 column matrix of residuals. If it is assumed that the expectation of u is 0, and that the expectation of uu' (u' is the conjugate of u) equals the variance times the identity matrix, and that X and Y have been centered and scaled so that the XX' and YY' are matrices of correlation coefficients, then there exists a matrix C, satisfying Eq. 2 $C'(XX')C = A$, and Eq. 3 $C'C = CC' = I$, where A is a diagonal matrix with ordered Eigenvalues of XX' on the diagonal. The columns of C are the normalized Eigenvectors.

A new set of explanatory variables Z may be formed by $Z = XC$. These are summarized as:

Eq. 4 $Y = X\beta = u = XCC'\beta + u = Za + u$, where the Z vectors are orthogonal. This process 48 of transforming the 'x' data into 'z' data produces a diagonal matrix A of Eigenvalues of the principal components. An Eigenvector of the square matrix A of order n is a nonzero vector X where $AX = \lambda X$, and the scalar $\lambda$ is called an Eigenvalue. Eigenvalues may be calculated for matrix A from Eq. 5:

Eq. 5 $|A - \lambda I| = 0$, where I is the identity matrix, and the corresponding Eigenvectors X may then be found by solving $(A - \lambda I)X = 0$. The Eigenvalues are sorted numerically from the largest (top left of the diagonal) to the smallest (bottom right). If strong multicollinearity exists, as it does for many of our explanatory variables, one or more of the lower right diagonal terms will be very small compared with the others and these terms may approach zero. If the Eigenvalue is sufficiently close to zero, the value of the corresponding 'z' transform of the 'x' data is also essentially zero:

Eq. 6 $Zk = Fk(x1, x2, \ldots, xn) = 0$, where Fk is the linear transform derived from PCA.

The relationships of Eq. 6 are used to test each M-L curve fit to determine whether the 'x' values obtained from M-L comport with those in the calibration set (derived from the known samples). Those Zk's which have sufficiently small Eigenvalues are selected to test the M-L results in step 50. A three to five sigma limit on the value of each thus selected Zk is used, and M-L solutions which result in Zk's which are outside this range are rejected as M-L fitting failures.

The orthogonal explanatory variables are used in the regression to determine a model equation 48. Since the Z variables are orthogonal, stepwise or other techniques are a reliable method for selecting terms for use in the regression model.

Figure 6B:
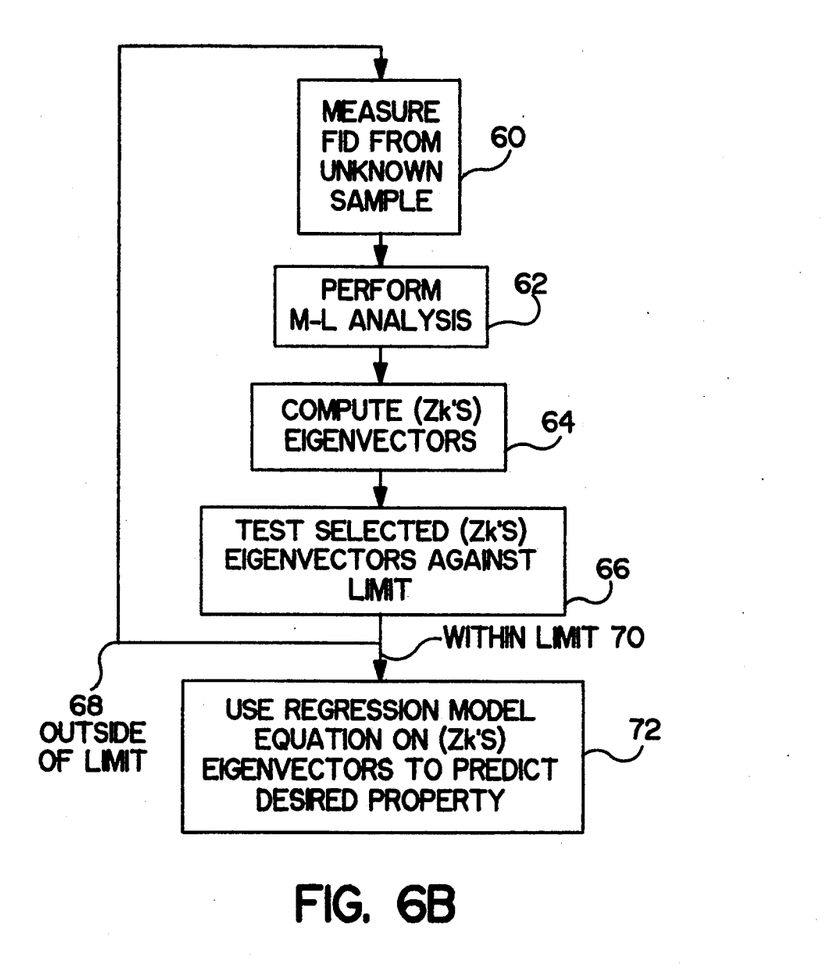

The calculated regression model equation is applied to an unknown sample via the flow chart of FIG. 6B. The FID 60 of the sample is measured and an M-L analysis is performed 62 from which the Eigenvectors (Zk's) are calculated 64. The selected Zk's (those with sufficiently small Eigenvalues) are tested against a deviation limitation 66, where the determinant of the vector divided by the standard deviation of that vector in the calibration data will cause a rejection of the M-L solution when the result is greater than 3, or in other preferred embodiments greater than 5 or 7.

Still referring to FIG. 6B, the Zk's for those M-L solutions which pass the limit test 70 are regressed via the model regression equation to predict the desired property 72. If outside this limit, M-L 62 is restarted with different starting assumptions and steps 64 and 66 repeated. Should repeated failures occur with a given sample, it is discarded, and a new sample is taken and the steps of FIG. 6A are repeated.

The parameters are calculated for the unknown, and these parameters with desired non-linear transforms are used in the regression equation to determine the actual type, property and quantity of target nuclei, including inherent viscosity, melt index or melt flow (related to average molecular weights) in plastics/polymers. Ratios are used since constants with dimensions of weight would require the samples to be carefully weighed before measuring.

Figure 7:
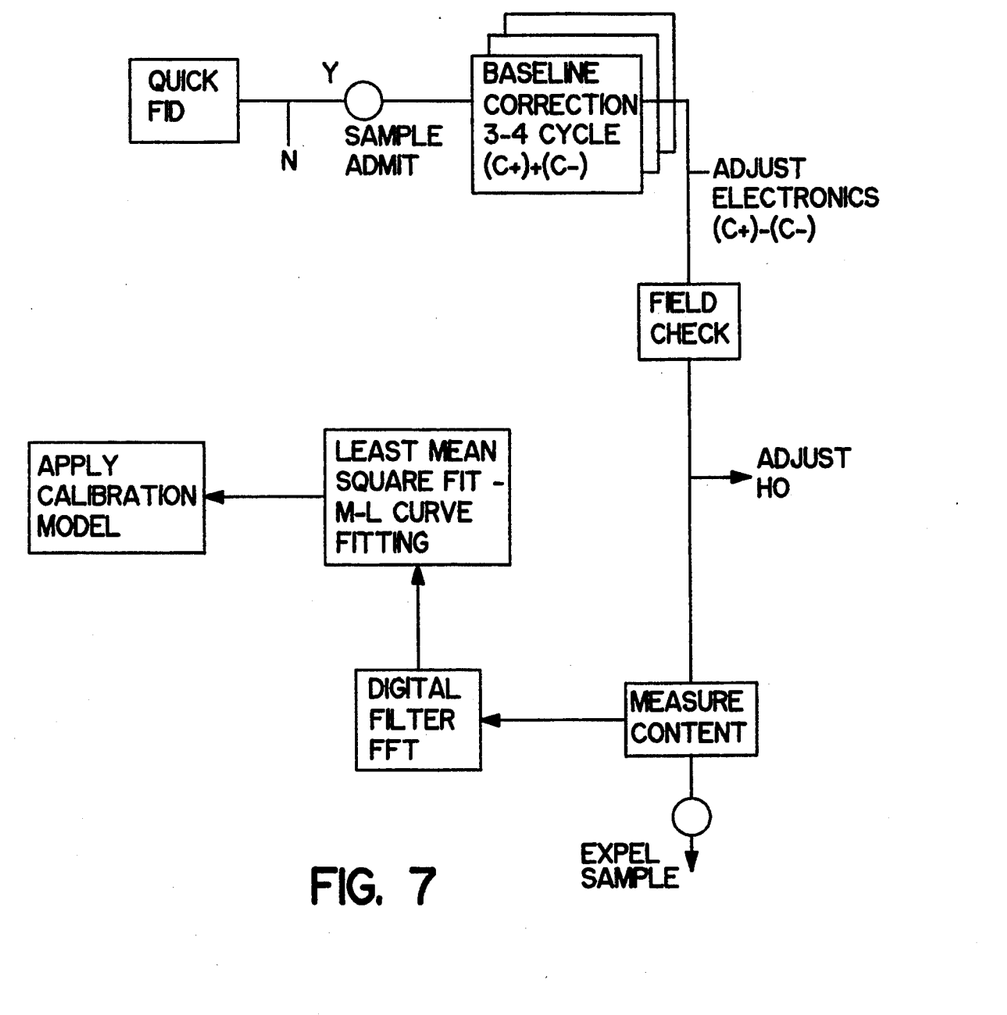
FIG. 7 is a flow chart of the steps to establish an effective industrial measurement.

FIG. 7 is a flow chart showing the steps of measurement to establish effective industrial measurement. A single FID curve is established to see if the sample area is clear (Quick FID) in an abbreviated cycle of attempting to establish an FID curve. If the sample region is not clear (N), measurement is interrupted to allow valve V2 to open and jets J and gravity to clear the region. A new Quick FID step establishes clearance. Then a new sample is admitted by closing valve V2, opening valve V1 and making such adjustments of probe P and line L1 as may be necessary to assure sample acquisition. Jets J adjust and stabilize the new sample.

An electronic signal processing apparatus baseline is established in 3-4 cycles (each having (+) and (−) sub-cycles with addition of (C+) and (C−) to detect a baseline offset and compensate for it). It would be feasible to avoid this baseline step determination and simply deal with it as an additional parameter (i.e. eleventh dimension in the M-L analysis, but this would increase iteration time).

Further adjustment is established by coils 124 to adjust H0 (i.e., resonance) and this is enabled by ten to twenty field check cycles of FID curve generation. The (C−) FID is subtracted from the (C+) FID, (this process eliminates small baseline offsets) to obtain a workable digitized FID signal—which has a maximum value at resonance. H0 is adjusted via coil current generator 117 and coils 124 until such maximum is achieved, and then H0 may be changed to offset the system by a given amount of about 0.1 to 3 KHz.

Then one or more (usually five to one hundred) measurement cycles are conducted to obtain a useable measurement. Each of these five to one hundred cycles involves a modulated transmission/reception/flash A-D conversion, and storage of data. The curves are then averaged for M-L curve fitting, and the above listed intercepts and ratios are established. Similar cycles, often somewhat abbreviated can be applied for Quick FID, field check and baseline correction purposes. Each of the sub-cycles [(+) and (−)] of each such cycle involves a capture and utilization of thousands of FID points in data reduction. Each sub-cycle occurs on the order of a second and the number of such sub-cycles employed depends on the desired smoothing and signal to noise ratio (S/N); generally S/N improves in a square root relationship to the number of cycles.

As noted in patents cited in the above section, cross Reference to Related Patents and Applications, sample tube composition can distort readings. If glass is not used (and it is preferred to avoid glass in industrial usage), then the replacement should not be a hydrocarbon plastic. But fluorocarbons can be effective in several applications since signals from fluorine appear far from resonance. These signals can be distinguished from hydrogen at the levels of sensitivity required and if desired can be filtered (or distinguished). In other cases of higher sensitivity measurements, e.g., for gauging relative proportions of amorphous and crystalline species in mixtures thereof, the sample container should be glass or non-protonic ceramic. In some instances, however, fluorocarbon or reinforced fluorocarbon can be used acceptably for polymer measurements. In all such cases the point is to avoid sample containers with species that can couple with transmitted energy and generate a FID decay curve mimicking the samples.

While "air" or "air curtain" are referred to above it will be understood that other gas or liquid environments can be utilized within the scope of the present invention.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Apparatus for measuring a selected polymer property from an on-line process, the property selected from the group consisting of viscosity, melt index, melt flow and melt flow ratio and doing so in essentially real time with samples of polymer from the process that are in solid state essentially throughout the period of handling within the apparatus, the apparatus comprising:
   (a) means for taking a series of samples from the process and stabilizing temperature of each sample at a level equal to or above mobility enhancing temperature thereof, but below melting temperature thereof, and
   (b) means for performing a nuclear magnetic resonance analysis of the sample by magnetic precession pulsing and acquisition of a free induction decay, extracting selected physical NMR properties, including relaxation rates, in an automatically performed analysis in a multidimensional regression model already correlated to a parameter selected from the group consisting of viscosity, melt index, melt flow and melt flow ratio, to extract such selected parameter as a measurement result, and
   (c) means for maintaining constant the selected temperature of (a) above throughout the FID data acquisition step of (b) above, for each sample.

2. The apparatus of claim 1 wherein said means (b) include means for performing a Principal Component Analysis (which entails establishing new orthogonal explanatory variables as linear combinations) of component variables of data acquired from the said decay as part of the regression to establish the regression model within the apparatus.

3. Measurement process for measuring a selected polymer property from an on-line industrial process, the property selected from the group consisting of viscosity, melt index, melt flow and melt flow ratio and doing so in essentially real time with samples of polymer from the process that are in solid state essentially throughout the period of handling in such measurement process, the measurement process comprising the steps of:
   (a) taking a series of samples from the process and stabilizing temperature of each sample at a level equal to or above mobility enhancing temperature thereof, but below melting temperature thereof, and
   (b) performing a nuclear magnetic resonance analysis of the sample by magnetic precession pulsing and acquisition of a free induction decay, extracting selected physical NMR properties, including relaxation rates, in an automatically performed analysis in a multidimensional regression calibration model already correlated to a parameter selected from the group consisting of viscosity, melt index, melt flow and melt flow ratio, to extract such selected parameter as a measurement result, and
   (c) maintaining the selected temperature of (a) above throughout the FID data acquisition step of (b) above, for each sample.

4. The measurement process of claim 3 wherein said means (b) include means for performing a Principal Component Analysis which entails (establishing new orthogonal explanatory variables as linear combinations) of component variables of data acquired from the said decay as part of the regression to establish the regression model within the apparatus.

5. The apparatus of claim 1 comprising means defining a first chamber for heating the extracted samples to the baseline temperature and a second chamber for conducting the nmr measurement and first and second independent means for sample temperature maintenance associated with said first and second chambers, respectively.

6. Process in accordance with claim 3 wherein the sample temperature is maintained constant by:
   (i) measuring the temperature of said sample,
   (ii) heating a volume of gas,
   (iii) circulating said heated gas around said sample measuring region and controlling said sample temperature responsive to said temperature measurement whereby said sample temperature is maintained about constant at the baseline.

* * * * *